(12) United States Patent
Beller et al.

(10) Patent No.: US 8,728,040 B2
(45) Date of Patent: May 20, 2014

(54) INJECTOR FOR AUTO-INJECTION OF MEDICATION AND ASSOCIATED METHOD OF USE

(75) Inventors: Thomas C. Beller, Hilton Head, SC (US); Mark Forman, Manalapan, NJ (US); Matthew J. Morton, Morrisville, NC (US); Amanda D. Bedsaul, Morrisville, NC (US)

(73) Assignee: TCB Medical Devices, LLC, Hilton Head, NC (US)

( * ) Notice: Subject to any disclaimer, the term of this patent is extended or adjusted under 35 U.S.C. 154(b) by 158 days.

(21) Appl. No.: 13/167,551

(22) Filed: Jun. 23, 2011

(65) Prior Publication Data

US 2011/0319864 A1 Dec. 29, 2011

Related U.S. Application Data

(60) Provisional application No. 61/357,618, filed on Jun. 23, 2010.

(51) Int. Cl.
*A61M 5/32* (2006.01)
(52) U.S. Cl.
USPC .............................. 604/198; 604/137; 604/197
(58) Field of Classification Search
USPC ........................... 604/110, 134–137, 196–198
See application file for complete search history.

(56) References Cited

U.S. PATENT DOCUMENTS

| 5,681,291 | A | 10/1997 | Galli |
| 5,928,197 | A | 7/1999 | Niehoff |
| 2005/0203466 | A1* | 9/2005 | Hommann et al. ........... 604/240 |
| 2007/0088268 | A1* | 4/2007 | Edwards ....................... 604/136 |
| 2008/0039789 | A1 | 2/2008 | Wyrick |
| 2008/0051715 | A1 | 2/2008 | Young et al. |
| 2010/0152655 | A1 | 6/2010 | Stamp |

* cited by examiner

*Primary Examiner* — Emily Schmidt
(74) *Attorney, Agent, or Firm* — Stroock & Stroock & Lavan LLP

(57) ABSTRACT

A key-shaped portable injector for delivering a dose of medication, the injector preferably including a cap, a body having an internal cavity, a syringe or cartridge with an attached needle within the internal cavity, a protective sleeve, an activation mechanism and a safety mechanism wherein the injector is reconfigurable from a first, non-deployed configuration where the activation mechanism, syringe or cartridge and a safety mechanism are all in a first position with respect to the body to a second, deployed configuration where the safety mechanism, activation mechanism, and syringe or cartridge are all in a second position with respect to the body and to a third, depleted configuration where the activation mechanism is back to its first position and a protective sleeve is in its second position.

42 Claims, 11 Drawing Sheets

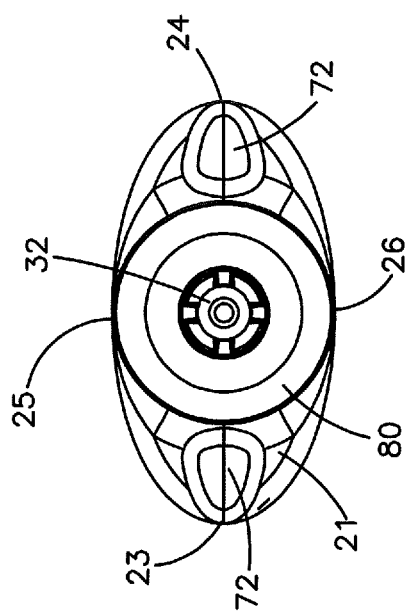
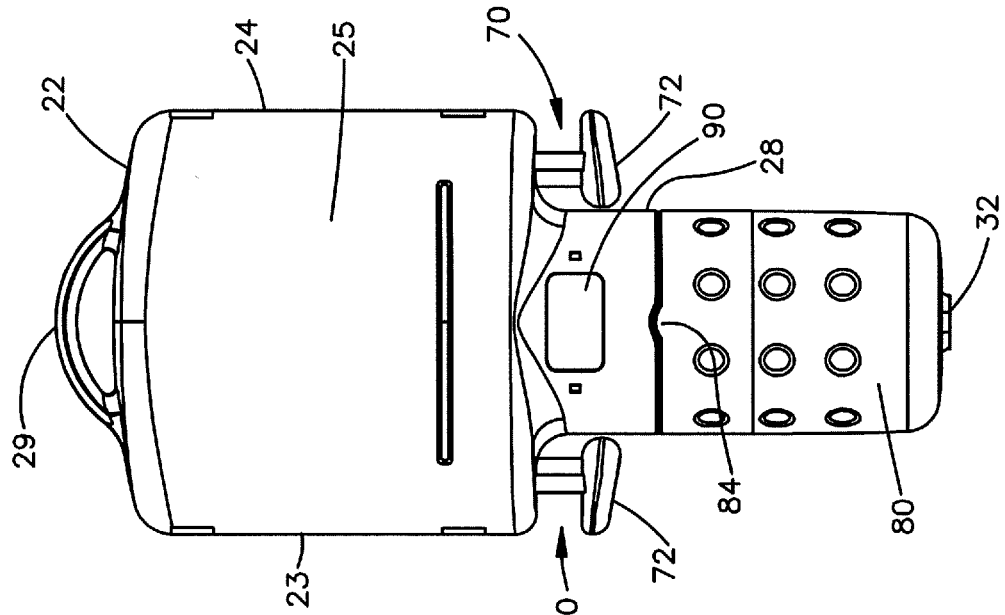
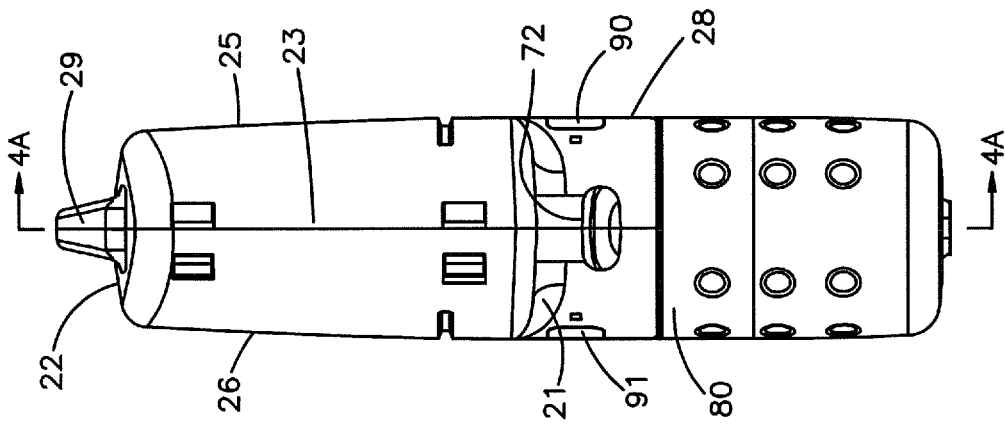
Fig.1E
Fig.1D
Fig.1C

INJECTOR FOR AUTO-INJECTION OF MEDICATION AND ASSOCIATED METHOD OF USE

CROSS REFERENCE TO RELATED APPLICATIONS

The present application claims priority to and the benefit of the filing date of U.S. Provisional No. 61/357,618, filed Jun. 23, 2010, which application is incorporated herein fully by this reference.

FIELD OF INVENTION

The present invention relates generally to an injector apparatus and method for the automatic injection of a liquid and, more specifically, to an injector requiring only one hand for use.

BACKGROUND OF THE INVENTION

Certain medical conditions require immediate injection of medication. Conditions requiring such treatment may result from a variety of causes. Among the most serious of those conditions is anaphylaxis (a severe allergic reaction) that, in many cases, can become fatal within minutes if left untreated. Numerous allergens may cause anaphylaxis including insect bites, medications, latex, foods and other various chemical substances. For example, food products having even small quantities of peanuts, seafood or milk products can, in some individuals, induce severe, potentially lethal reactions. In foods, the allergen may be "hidden", that is, the food unknowingly, may contain a minute trace of an allergenic ingredient or may have been exposed to the allergenic ingredient during its processing. When anaphylaxis occurs, often there is insufficient time for the patient to reach a hospital or other trained and equipped medical personnel.

Individuals known to be at risk for anaphylaxis typically are advised to carry, at all times, an auto-injector apparatus adapted to deliver a dose of Epinephrine. The ability to inject the Epinephrine immediately can be a matter of life or death. Notwithstanding the severe risk involved, there is evidence that a large proportion of the population that should be carrying such an apparatus, in fact, does not. Moreover, even for those individuals that carry such an apparatus, it has been reported that a large proportion are insufficiently familiar with its use and operation.

The most common automatic emergency Epinephrine injector apparatus is the EPIPEN® auto-injector distributed by Mylan, Inc. The EPIPEN® injector is designed to rapidly inject an adult dose of about 0.30 milligrams of Epinephrine. The injector is about six inches long and has an oval tubular shape with a diameter of approximately three inches. The injector is relatively bulky and requires training to be administered correctly since proper use of the device is not intuitive. As a patient may only use the injector infrequently, there may be some confusion in performing the required manipulative steps, particularly when the individual experiencing anaphylaxis may be in a state of panic. Furthermore, should it be necessary for someone other than the patient (e.g., a bystander) to administer the medication, that person may not know how to operate the injector. Additionally, some injectors possess complicated parts requiring multiple hands for proper use and administration. Consequently, precious time may be lost, increasing the risk to the patient. Moreover, confusion has been reported regarding which end of the device the needle protrudes from and, as such, accidental injections into the thumb or finger of the person delivering the medicine are common. Additionally, after the injector has been used to effect an injection, its hypodermic needle often remains exposed, presenting post-injection hazards. Among such hazards are those associated with accidental stabbing or puncture injuries, or the spread of blood born diseases such as HIV and hepatitis B and C.

It would be desirable to provide a more compact, easier to use injector, which patients are more likely to carry on their person, for rapid transcutaneous administration of a predetermined dose of medication. It would also be desirable to provide an injector which can be unlocked, activated, and administered with the use of only one hand.

BRIEF SUMMARY OF THE INVENTION

In certain embodiments, the injector includes a generally rectangular shaped body having an extension or stem extending from a first, forward facing surface thereof. In alternate embodiments the body is generally square, oval or other shape dimensioned to fit within a user's hand, with the extension or stem extending from a forward facing surface thereof. As such, the injector is substantially key-shaped and is configured to fit in the palm of a user's hand such that the body may be held within the user's hand with the extension extending between the index and middle fingers. A depressible safety button on each side of the extension also extend from the first surface of the body and are thus operative to be depressed (simultaneously or otherwise) by the index and middle fingers of the user. Thus, a user may hold the injector in one hand, simultaneously depressing the safety buttons with the same hand, thereby activating the injector. By depressing the injector against the user's skin at an injection site, the user engages an activation mechanism, and the injector is deployed, causing the syringe housed within the body to move towards the injection site, the point of the corresponding needle to extend beyond the body and pierce the user's skin and the liquid to be injected by virtue of a plunger. Post-deployment, when the user removes the injector from the injection site, a protective sleeve automatically extends from the extension to cover the needle point, which would otherwise extend beyond the body. Thus, in a post-deployment state, the injector automatically protects against inadvertent puncture wounds from the needle A first preferred embodiment of the present invention is directed to a key-shaped portable injector for delivering a dose of medication. The injector may preferably include a cap, a body having an internal cavity, a syringe or cartridge (hereinafter "syringe") located within the internal cavity for storing the medication, a needle extending from the syringe, a protective sleeve, an activation mechanism, a power assembly that may include a spring-containing plunger arm and a crown, and a safety mechanism. In one embodiment of use, the injector is reconfigurable from a first, non-deployed configuration, to a second, deployed configuration, and a third depleted configuration. The activation mechanism, the syringe, and the plunger arm are all moveably located with respect to the body from the first, non-deployed position to a second, deployed position. The crown does move, but changes shape from a non-deformed shape when the activation mechanism is in its first position to a deformed shape when the activation mechanism is in its second position. The activation mechanism, the syringe, the plunger arm and the protective sleeve are all in their first positions when the injector is in the first, non-deployed configuration and are in their second positions when the injector is in the second, deployed configuration. The crown is in its non-deformed shape when the injector is in its first, non-deployed configuration and in its deformed shape when the injector is in its deployed configuration. The safety sleeve may be moveably located with respect to the activation mechanism. The safety sleeve is in its first position when the device is in the non-deployed configuration and in its second position when the device is in the depleted configuration. While in the deployed configuration, the activation sleeve is in a transitional position between its first and second positions. While in the non-deployed configuration, the crown of the power assembly prevents the plunger arm from moving to its second position. The safety mechanism is also moveably located with respect to the body from a first, safety position to a second, ready position. In the first position, the safety mechanism prevents the crown from deforming thus preventing the release of the plunger arm. By preventing the crown from deforming, the safety mechanism also prevents the activation member from moving to its second position.

A second preferred embodiment of the present invention is directed to a portable injector for delivering a dose of liquid. The injector may preferably include a device body, a liquid-containing syringe, a needle, a spring-activated plunger arm, a protective sleeve, an activation mechanism and safety mechanism. The device body comprises a forward facing surface, a trailing surface, a first side surface, a second side surface, a top surface and a bottom surface wherein the forward facing surface, the trailing surface, the first side surface, the second side surface, the top surface and the bottom surface define an internal cavity. The liquid containing syringe may be preferably located within the internal cavity of the body and when activated, allows the needle to extend from the forward facing surface of the body.

The protective sleeve is moveably located with respect to the activation mechanism. In the first position, the sleeve is located within the activation mechanism towards its distal, back end while the device is in its non-deployed configuration. This position allows for exposure of the needle when the device is in the deployed configuration, facilitating exposure of the needle. The sleeve preferably moves from a first position to a second position. From the first position, the sleeve may preferably extend proximally from the forward facing surface of the device body into its second position to encase the needle as it is removed from the injection site after deployment. More preferably, the protective sleeve may be biased so that after injection of the liquid and removal of the needle from the patient's skin, the sleeve may automatically move to its second position to protect the user from accidental needle stick. In its first position, the protective sleeve may preferably interact with or engage the activation member so that it is prevented from moving to its second position until the activation member has moved to its second position. In its second position, the protective sleeve preferably interacts with or engages the activation member in a second way so that the sleeve may be locked or secured in the second position.

In one embodiment, the activation mechanism is moveably located with respect to the device body from a first position to a second position. The protective sleeve is contained within the activation mechanism when the device is in the non-deployed (i.e. pre-deployment) configuration.

The safety mechanism is also moveably located with respect to the device body. The safety mechanism may move from a first position to a second position. In the first position, the safety mechanism prevents the crown from deforming, which secondarily prevents movement of the activation mechanism.

The injector is preferably in the shape of a key. In another embodiment, the injector is preferably in the shape of a modern, battery containing, key-chain.

The injector contains a syringe that is attached to a needle. The syringe is preferably filled with liquid, which is prevented from exiting the non-needle-containing end of the syringe by a rubber plunger. The rubber plunger may be moveably located within the syringe from a first position to a second position. In its first position, the rubber plunger is displaced from the needle-containing end of the syringe, leaving space for the liquid. In its second, deployed position the rubber plunger moves closer to the proximal, needle-containing end of the syringe, leaving less space for liquid. The rubber plunger may be threadably attached to the plunger arm. The syringe and the attached needle, are preferably in operative association with the plunger arm so that the syringe, and the attached needle are moveable with respect to the body from a first position in which the injector is in the first, non-deployed configuration, to a second position in which the injector is in the second, deployed configuration. When moving from the first position to the second position, the syringe and the attached needle is capable of moving in a proximal direction.

The injector may also contain a power assembly that interacts with the syringe. The power assembly may comprise a crown, and a hollow plunger arm containing a spring. The plunger arm may be moveably located within the syringe. The plunger arm is preferably moveable from a first position, when the injector is in the first, non-deployed configuration, to a second position, when the injector is in the second, deployed configuration. When in its first position, the plunger arm preferably contains a compressed spring. The plunger arm extends proximally to its second position when it is separated from the crown during activation of the device. When the device is in the non-deployed configuration, the crown interacts with or engages the plunger arm, preventing the plunger arm from moving from its first position to its second position. The crown is preferably shaped like a hat with a brim on either side. Movement of the activation member into its second, deployed position, causes the crown to deform by widening and flattening, allowing it to release the plunger arm, which in turn allows expansion of a spring. Expansion of the spring preferably causes the plunger arm to force the syringe and the attached needle, proximally towards the forward facing surface of the body. Movement of the plunger arm into its second, deployed position may push the plunger proximally within the syringe, releasing the liquid in the syringe thru the needle.

The safety mechanism may also comprise a pair of depressible buttons. More preferably, the depressible buttons may protrude proximally from the forward facing surface of the body and are located one on either side of the needle. The depressible buttons may be configured so that they must be simultaneously depressed in order for the crown to deform and for the activation mechanism to move from its first position to its second position.

The depressible buttons of the safety mechanism contain distal ends that are preferably in contact with the peripheral portion of the crown of the power assembly. In the first, safety position, the depressible buttons prevent the crown from deforming by obstructing its peripheral edges. The peripheral edges of the crown, when immobilized by the safety buttons, prevent the activation mechanism from moving from its first position to its second position.

The activation mechanism preferably includes a distal portion that resides in the internal cavity of the body. The distal portion of the activation mechanism interacts with the crown of the power assembly. In its first position, the activation mechanism may preferably be in close proximity to the crown or rest against the crown. In its second position the activation mechanism causes the crown to deform, releasing the plunger arm. The activation mechanism is prevented from moving to its second position when the safety mechanism is in its first, safety position, because the safety mechanism prevents the crown from deforming. After the plunger arm has been released and the syringe has moved to its second position, the activation mechanism may move back to its first, proximal position to facilitate the encasement of the needle along with the sleeve.

BRIEF DESCRIPTION OF THE DRAWINGS

The foregoing summary, as well as the following detailed description of the preferred embodiments of the application will be better understood when read in conjunction with the appended drawings. For the purposes of illustrating the injector of the present application, there is shown in the drawings preferred embodiments. It should be understood, however, that the application is not limited to the precise arrangements and instrumentalities shown. In the drawings:

FIG. 1C is a side view of the injector shown in FIG. 1A;

FIG. 1D is a top view of the injector shown in FIG. 1A;

FIG. 1E is a front view of the injector shown in FIG. 1A;

DETAILED DESCRIPTION OF EMBODIMENTS OF THE INVENTION

Figure 1A:
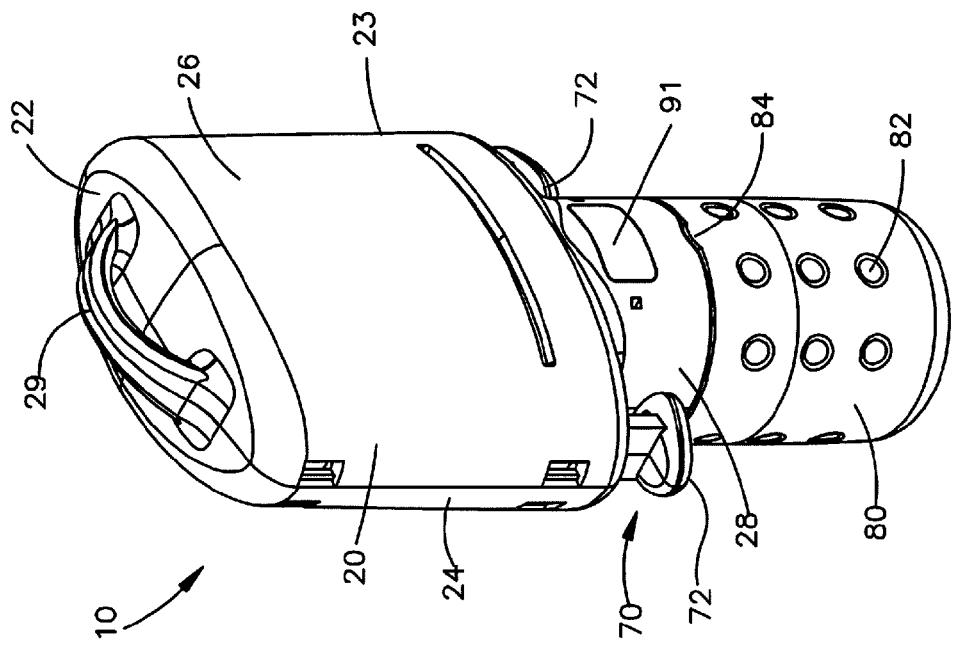
FIG. 1A is a perspective view of an injector according to a first embodiment of the present invention.
Figure 1B:
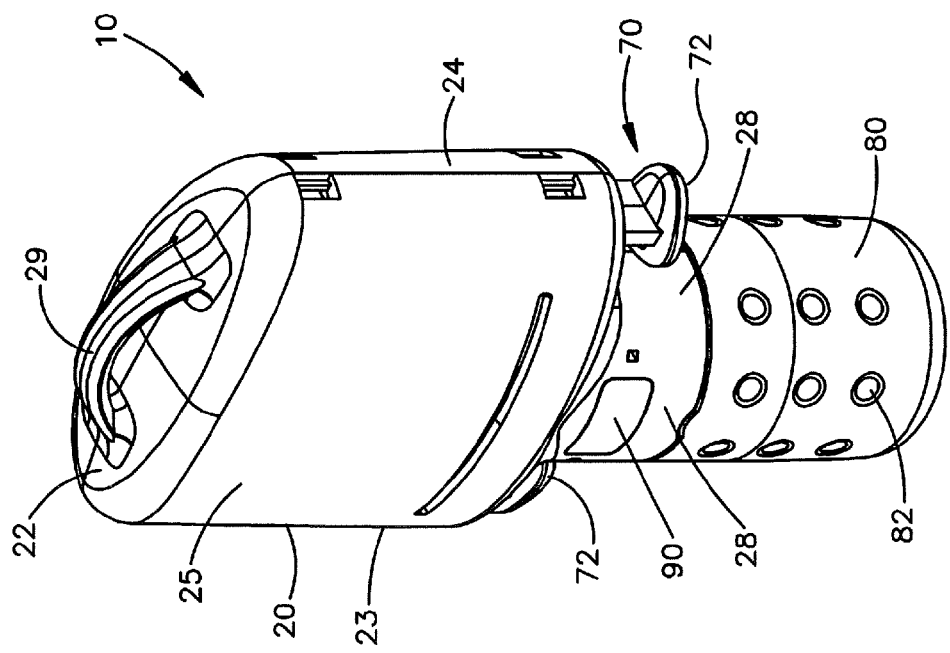
FIG. 1B is an alternate perspective view of the injector shown in FIG. 1A.

Certain illustrative embodiments of the invention will now be described with reference to the drawings. In general, such embodiments relate to embodiments of an apparatus for injecting a dose of medication, more specifically, a disposable, portable injector for administering a single dose of Epinephrine in an emergency situation. It should be understood however that the invention may have other applications and uses and should not be limited to the structure or use described and illustrated. For example, the injector apparatus may be used to administer other liquids or medication aside from Epinephrine. In addition, the injector apparatus may be designed to be reusable, etc.

Turning first to the embodiment of FIGS. 1A-E as will be described in greater detail below, the injector 10 preferably includes a body 20, a syringe or cartridge (hereinafter "syringe") 30 with attached needle 31, a power assembly 40, a protective sleeve 50, an activation member 60, and a safety mechanism 70 for providing a safety feature against accidental activation of the injector 10. The injector 10 may also include a cap 80 for providing additional assurance against accidental discharge.

The injector 10 is preferably sized and configured to be compact and may have a low profile. More preferably, referring to FIGS. 1A-1E, the injector 10 may be in the shape of a key, although other shapes are envisioned. As such, the injector 10 may be configured to reside on a keychain to facilitate portability. For example, the injector 10 may include a quick disconnect mechanism (not shown), such as a quick disconnect ring as commonly known in the art, to enable the injector 10 to be attachable and/or detachable from a key ring.

The device body 20 may include a forward facing surface 21, a trailing surface 22, a first side surface 23, a second side surface 24, a top surface 25 and a bottom surface 26. The surfaces 21, 22, 23, 24, 25, 26 define an internal cavity 27. The body 20 preferably also includes a stem 28 extending from the forward facing surface 21. The body may also comprise a partial loop 29, preferably on the trailing surface 22 to permit easy interaction with a ring or keychain. In one embodiment, the body is manufactured from polypropylene or an equivalent plastic material. Alternatively, the body 20 may be manufactured from any other material now or hereafter known for such purpose including, but not limited to, an acrylonitrile butadiene styrene (ABS) plastic resin. Preferably, the material may be selected such that the liquid/medication does not interact with the body 20 of the injector 10.

In one embodiment, the body 20 or stem 28 includes at least one window or multiple windows 90, 91 that allow for visual inspection of the syringe and the liquid/medication inside. The window 90, 91 may enable the user to verify that the liquid or medication is available, to determine if delivery of the liquid or medication has been made, and/or to provide the user with an indication whether the injector 10 has been used previously. For example, in one embodiment when the injector 10 is in an unused state, the window 90, 91 may be green, while after use, the window 90, 91 may turn red to indicate that the injector 10 has been used and should be discarded. It should be understood by one of ordinary skill in the art that other colors and/or other mechanisms may be used. For example, in another embodiment the window 90, 91 may display words or text instead of colors, etc. Additionally and/or alternatively, the window 90, 91 may simply show the level of the liquid remaining in the injector 10. As shown, the window 90, 91 may be located in one of the top and bottom surfaces 25, 26 although, as will be appreciated by one of ordinary skill in the art, the window 90, 91 may be located anywhere on the body 20 of the injector 10.

The syringe 30 (shown in FIGS. 4A-C) is configured to be located within the internal cavity 27 of the body 20. The syringe is preferably made of glass although other materials, such as cyclic olefin copolymer, polypropylene or other plastic or non-plastic materials are envisioned. The syringe 30 contains an attached needle 31, a plunger 32, wherein the plunger may be made of rubber, which prevents the liquid from exiting the needle-free end of the syringe. In one embodiment, the body 20 is sized and configured to hold approximately 0.3 mg of Epinephrine, although the syringe 30 may be sized and configured to hold other liquids, medications, etc. and may be larger or smaller depending on the desired quantity of liquid to be held. Preferably, the syringe 30 is a standard size to facilitate manufacture and filling and the body thickness is sized to accommodate it.

Figure 4A:
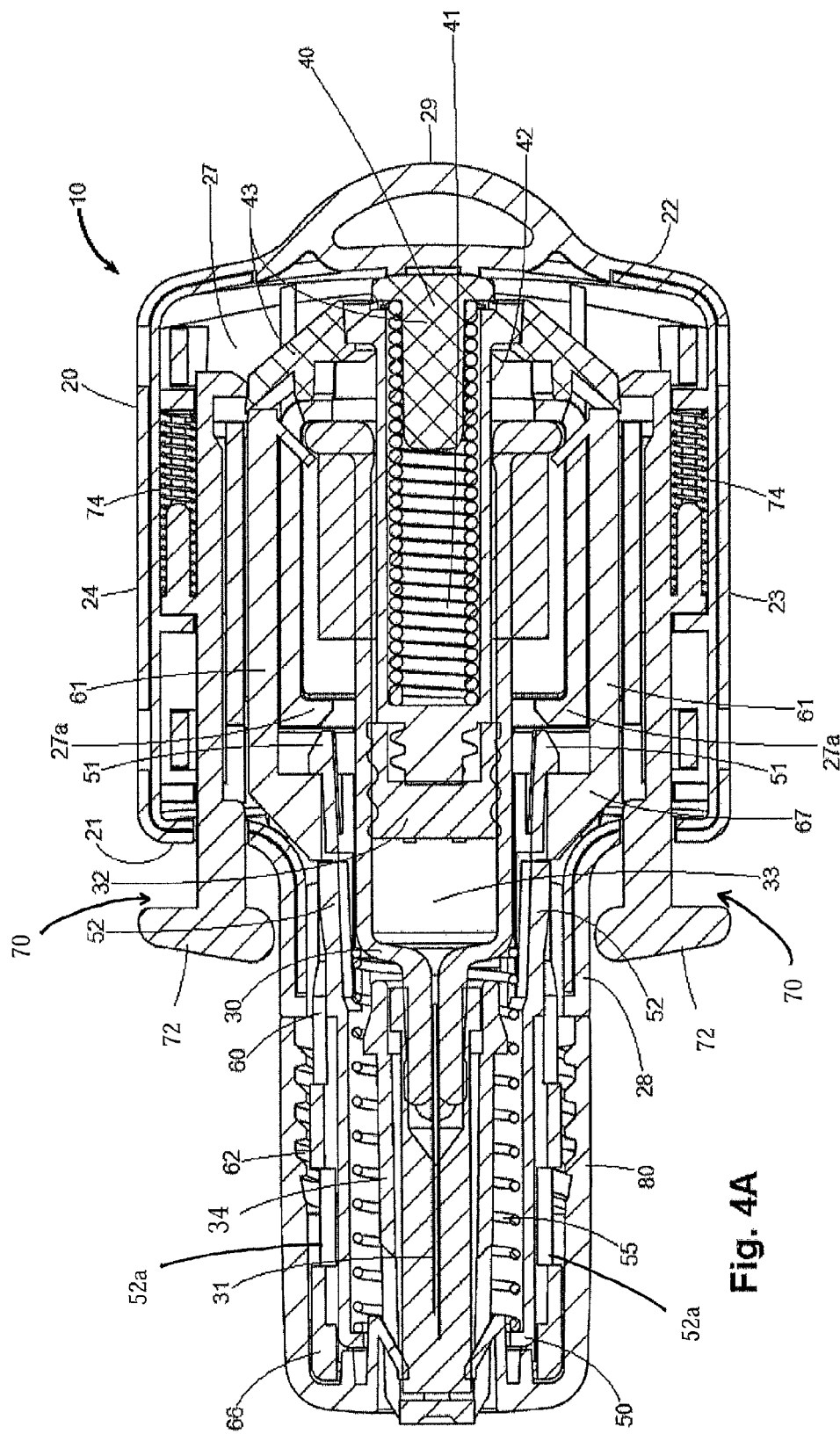
FIG. 4A is a cross-sectional view of the injector along line 4A-4A in FIG. 1C, the injector illustrated in a first, pre-deployed configuration.
Figure 4B:
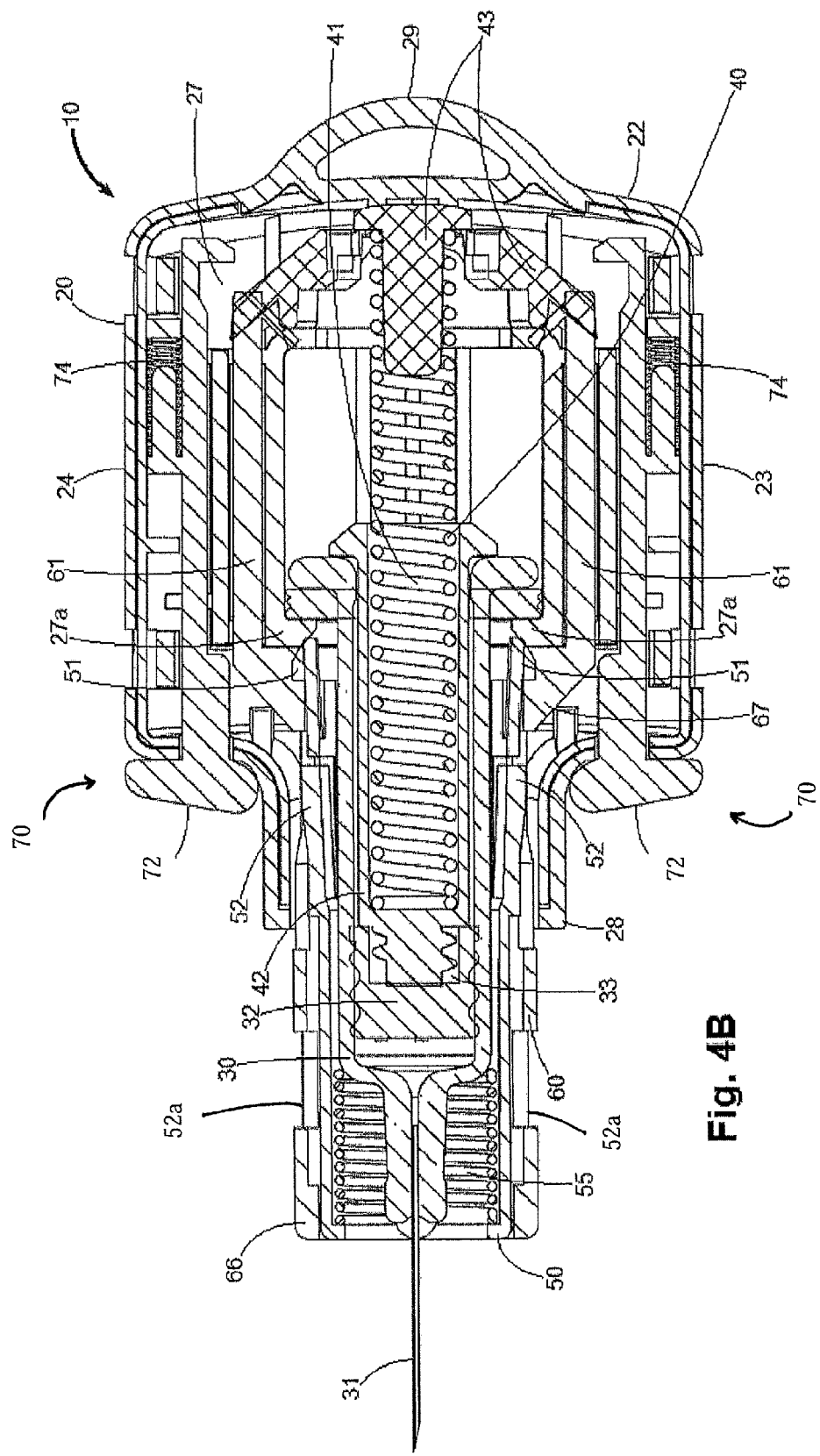
FIG. 4B is a cross sectional view of the injector along line 4A-4A in FIG. 1C, the injector illustrated in a second, deployed configuration.
Figure 4C:
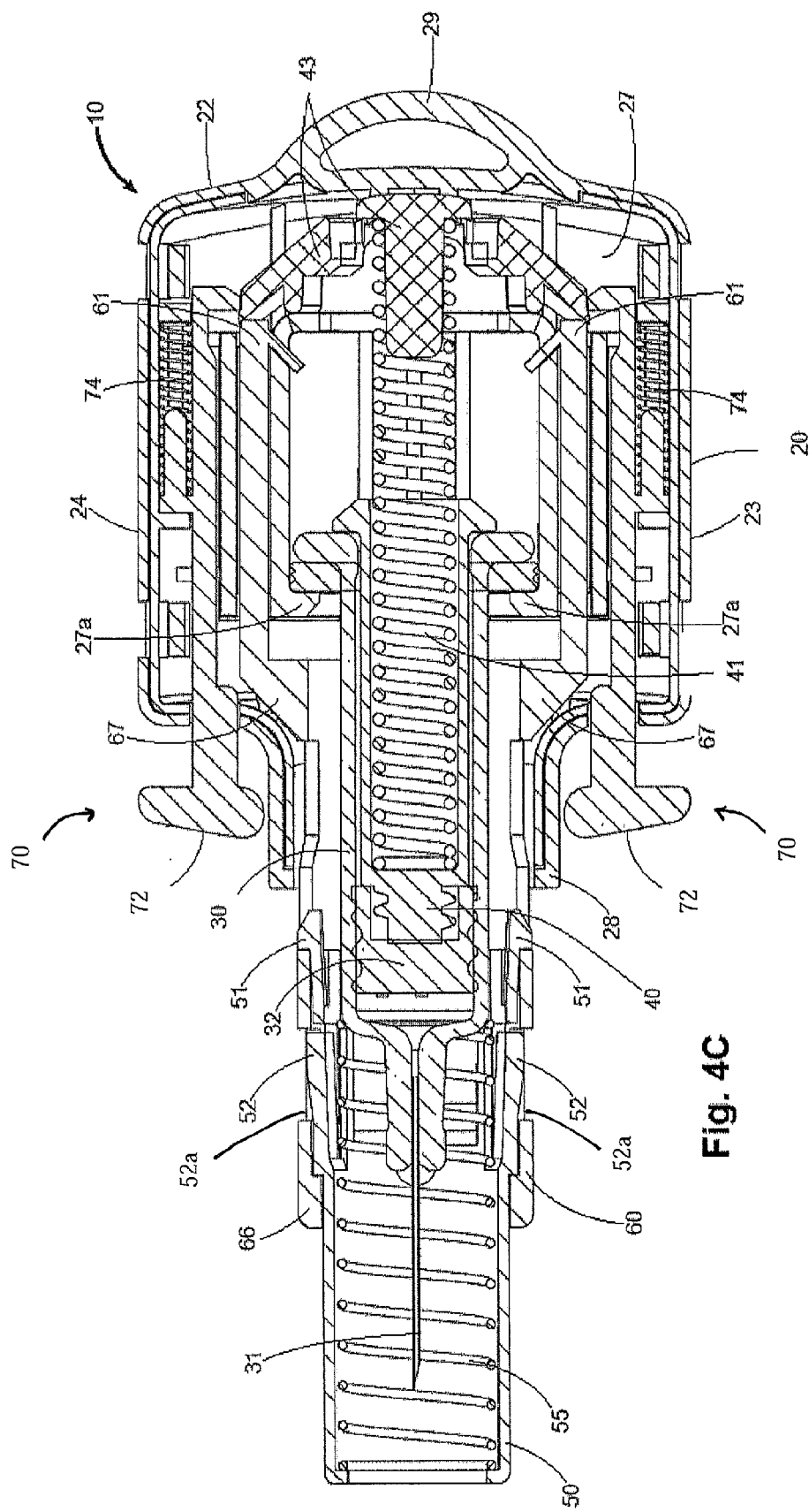
FIG. 4C is a cross-sectional view of the injector along line 4A-4A in FIG. 1C, the injector illustrated in a third, post-deployed configuration.
Figure 5:
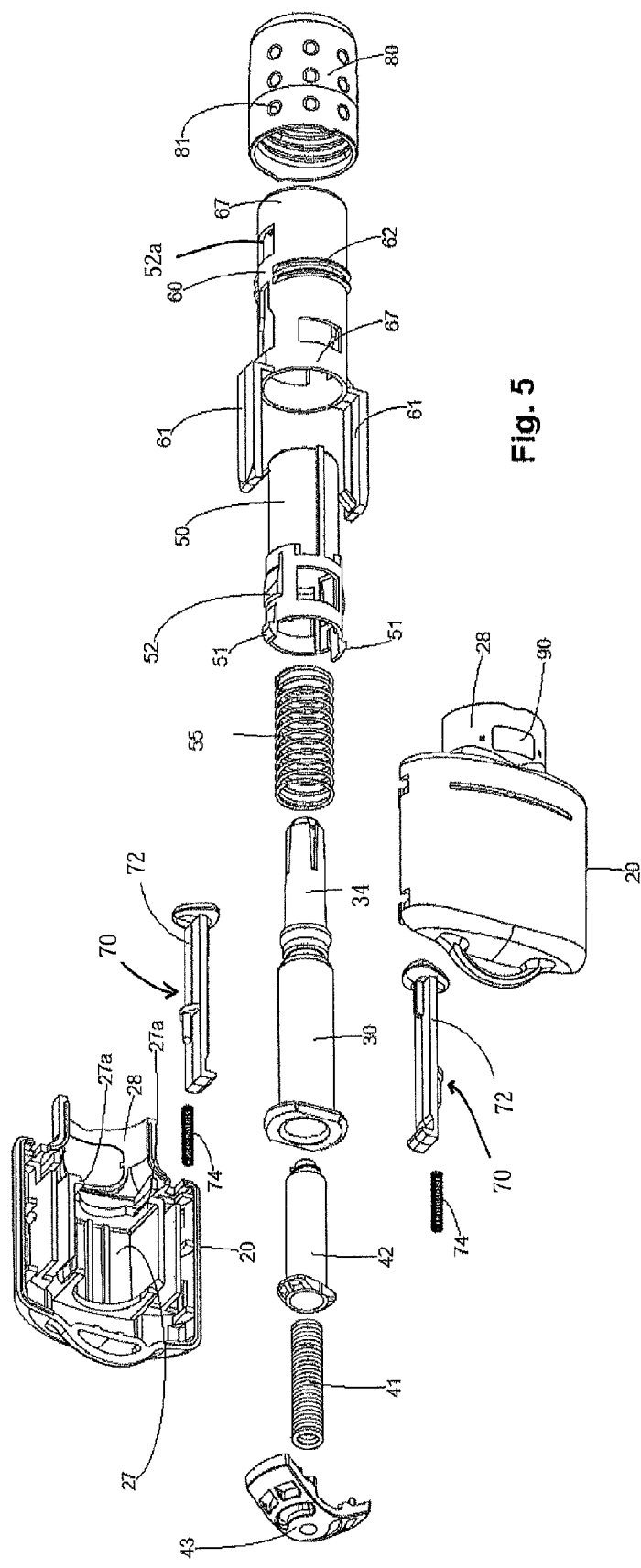
FIG. 5 is an exploded view of the injector of FIG. 1A.
Figure 6D:
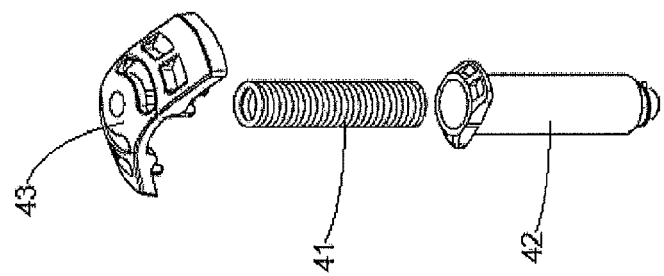
FIG. 6D is a perspective view of the power assembly of FIG. 6A, unassembled.
Figure 6B:
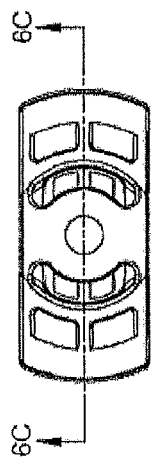
FIG. 6B is a trailing view of the preferred power assembly, of the injector of FIG. 1A.
Figure 6C:
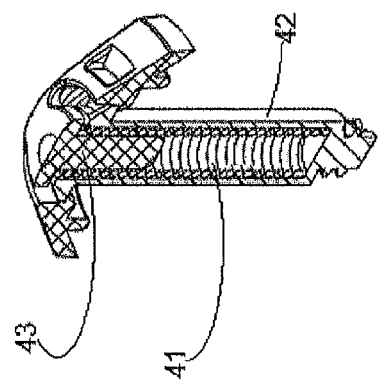
FIG. 6C is a cross-sectional perspective view of the power assembly along line 6C-6C in FIG. 6B.
Figure 6A:
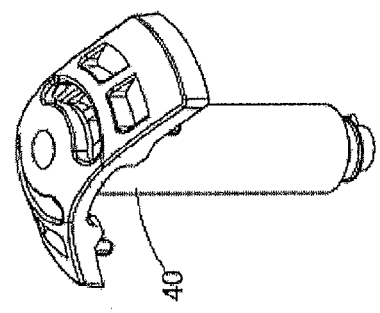
FIG. 6A is a perspective view of the preferred power assembly, of the injector of FIG. 1A.
Figure 7A:
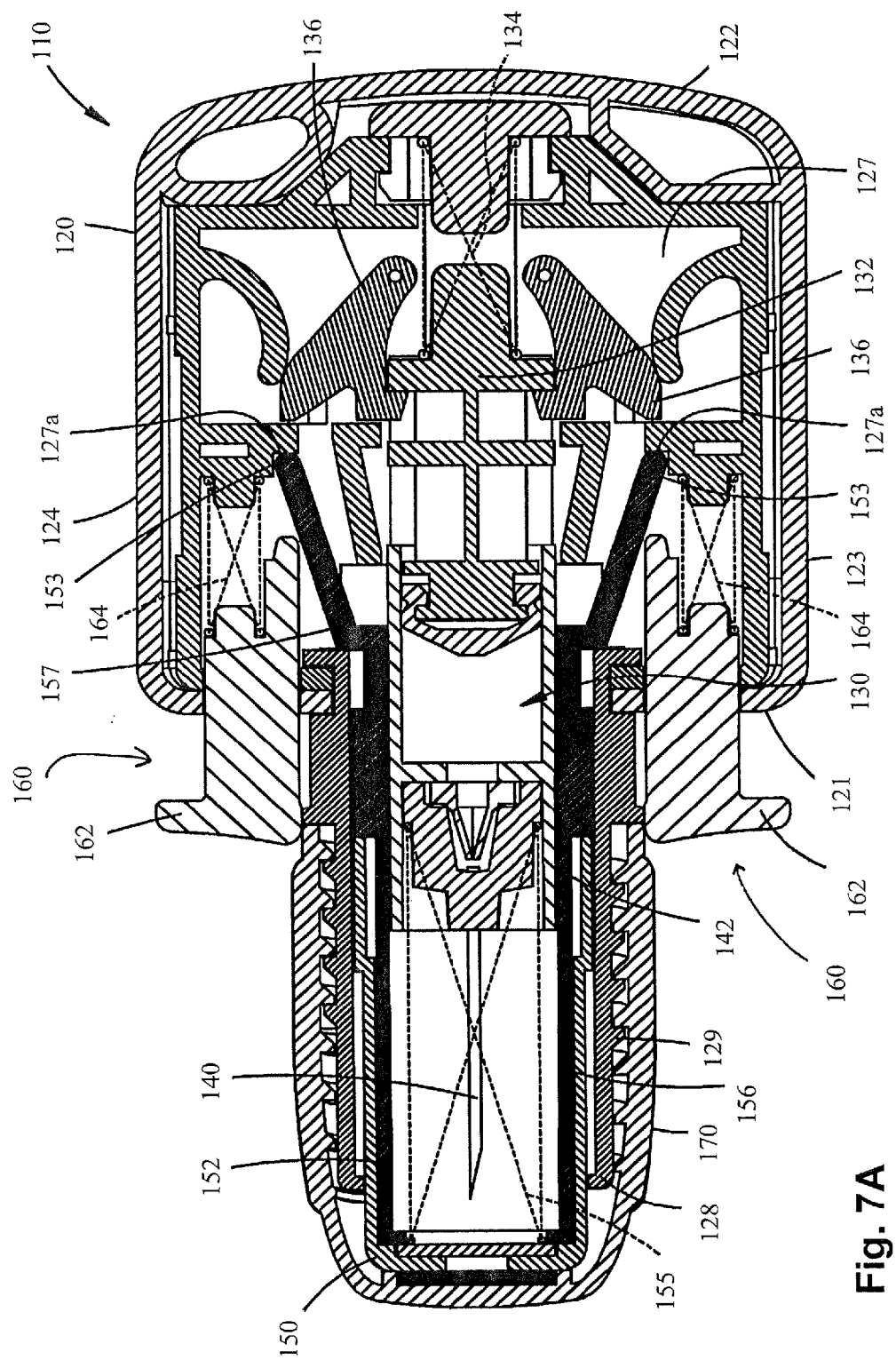
FIG. 7A is a cross-sectional view of an injector, in a first, non-deployed configuration, according to an alternate embodiment of the present invention.
Figure 7B:
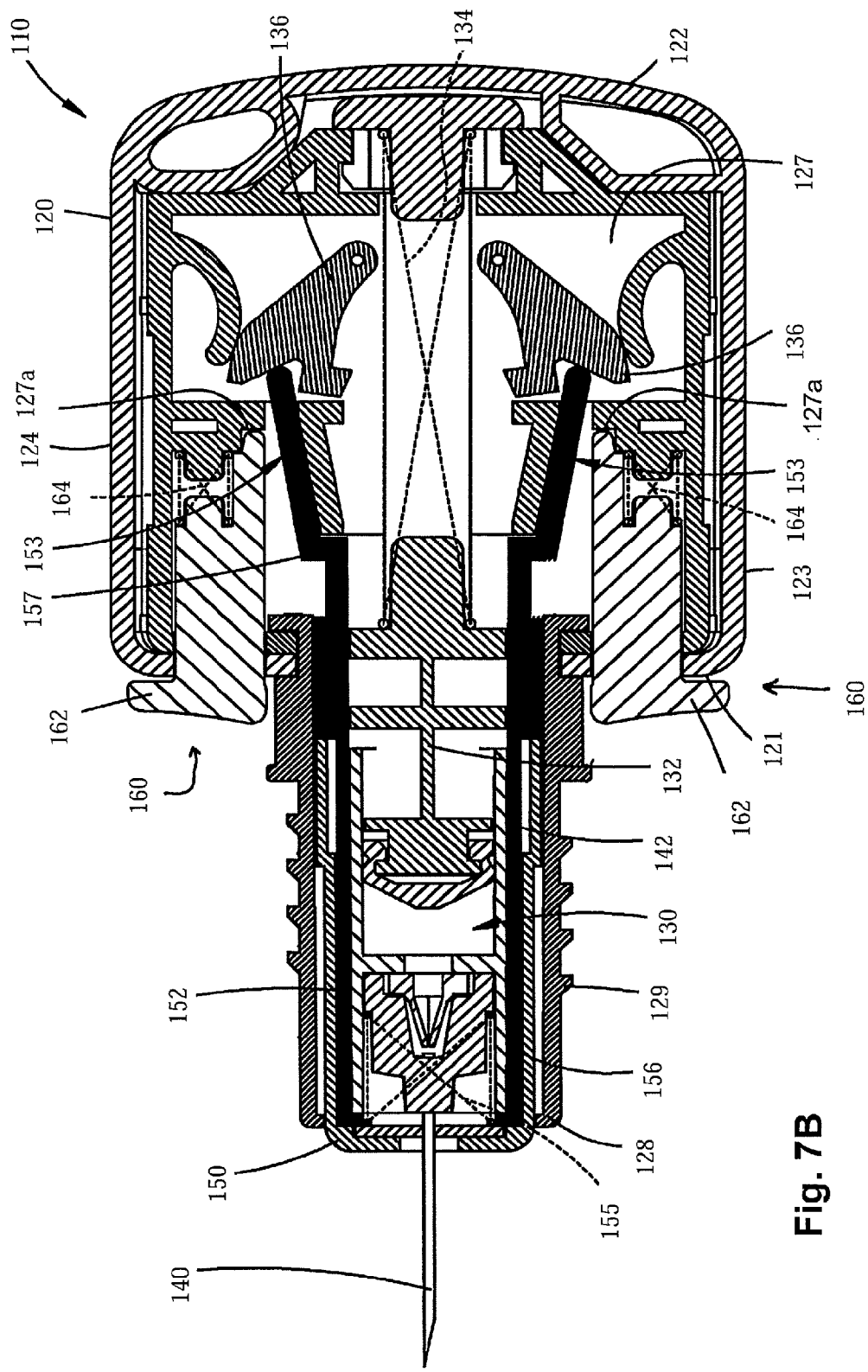
FIG. 7B is a cross-sectional view of the injector of FIG. 7A in a deployed configuration.
Figure 8A:
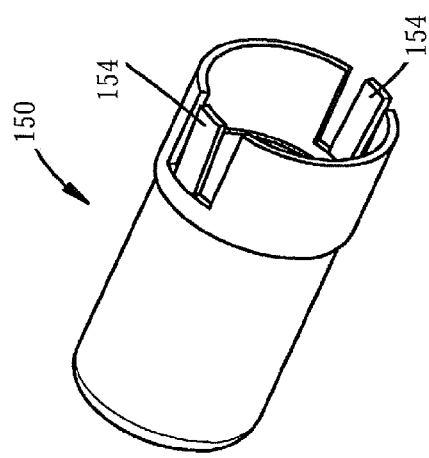
FIG. 8A is a perspective view of a sleeve used in connection with the injector shown in FIGS. 7A-7B.
Figure 8B:
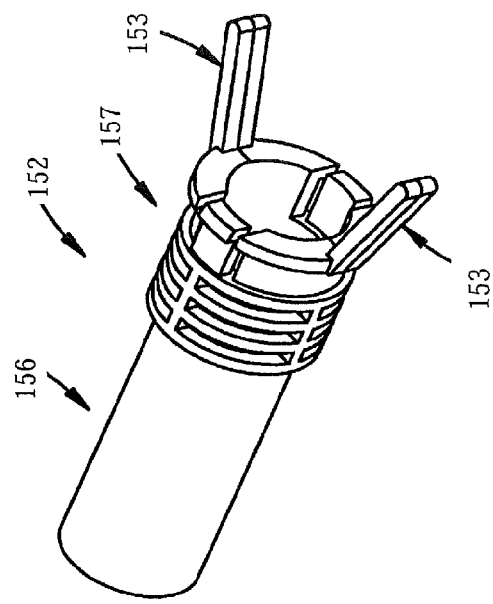
FIG. 8B is a perspective view of an activation member used in connection with the injector shown in FIGS. 7A-7B.

Referring to FIGS. 4A-C, as will be described in greater detail below, the liquid containing syringe may be operatively associated with a plunger arm 42, which is preferably part of the power assembly 40. The plunger arm 42 is moveably located with respect to the body 20 and the syringe 30. More preferably, at least a portion of the plunger arm 42 is moveably located within the syringe 30. The plunger arm 42 may be moveably located from a first position (as shown in FIG. 4A) in which the injector 10 is in the first, non-deployed (or pre-deployed) configuration to, a second position (as shown in FIG. 4B), in which the injector 10 is in the second, deployed configuration. More preferably, the syringe 30 and the attached needle 31 are capable of moving proximally, away from the trailing surface 22 of the body 20, into the second position by virtue of the force of the first spring 41. That is, advancing the plunger arm 42 proximally, to its biased position away from the trailing surface 22 of the body 20, causes the plunger arm 42 to push the plunger 32, which is in contact with the syringe 30 and liquid/medication 33, and hence advances the syringe 30 and the attached needle 31 proximally to expose the needle point and, in use, pierce the user's skin at the injection site. Advancing the plunger arm 42 proximally, also causes the plunger 32 to move proximally within the syringe 30 leaving diminishing space for the liquid/medication 33 and causing the liquid/medication 33 to eject through the tip of the needle 31.

Referring to FIGS. 4A-C, 5 and 6A-D the power assembly 40 may comprise a first spring 41, a plunger arm 42, and a crown 43. The first spring 41 preferably fits within (or in alternate embodiments around) the plunger arm 42 allowing the overall injector assembly to be smaller and thus better able to fit within the user's palm and/or pocket, etc. When the injector 10 is in the non-deployed configuration, the first spring 41 is in a compressed configuration within the plunger arm 42. Moreover, when the injector is in the non-deployed configuration, the crown 43 interacts with and engages the plunger arm 42 preventing the plunger arm 42 from moving proximally into its second position and also preventing the first spring 41 from expanding. Deforming of the crown 43 causes the plunger arm 42 to disengage allowing the plunger arm 42 to be moved proximally towards the forward facing surface 21 of the body 20 by the first spring 41, which is thus allowed to expand.

The needle 31 extends away from the trailing surface 22 of the body 20. More preferably, as shown, at least a portion of the needle 31 may be located within the stem 28. The needle 31 is preferably a 25-gauge needle having an exposed minimum length of 1.5 cm. However, it should be understood that the needle 31 may be thicker, thinner, longer or shorter, as appreciated by one of ordinary skill in the art. In alternate embodiments, the needle dimensions may vary depending on the characteristics of the user, for example the user's body mass, and/or the liquid, for example viscocity. The needle 31 is preferably in operative contact with a syringe 30, which is in operative contact with a plunger 32. The plunger 32 is preferably in operative contact with a plunger arm 42. The syringe 30 and the attached needle 31 are moveably located with respect to the body 20 from a first position (as shown in FIG. 4A) in which the injector 10 is in the first, non-deployed configuration to a second position (as shown in FIG. 4B), in which the injector 10 is in the second, deployed configuration. More preferably, the syringe 30 and the needle 31 are capable of moving proximally, away from the trailing surface 22 of the body 20, into the second position in response to activation of the first spring 41. That is, advancing the plunger arm 42 proximally, away from the trailing surface 22 of the body 20, causes the plunger arm 42 to advance the syringe 30, which is in contact with the needle 31, and hence advances the syringe 30 and the needle 31 proximally. In alternate embodiments, the needle 31 may be configured to remain stationary such that only the plunger arm 42 advances proximally within the syringe 30 to thereby release the liquid or medication.

The activation member 60 and the sleeve 50 preferably encase the needle 31 to protect the user from accidentally contacting the needle 33 before discharge of the liquid/medication 33. The sleeve 50 is operatively associated or coupled to the activation mechanism or member (interchangeably referred to herein) so that the movement of the activation member 60 may result in movement of the sleeve 50, as will be described in greater detail below. The activation member 60 and the sleeve 50 are preferably 2 separate pieces. More preferably, the sleeve 50 may be able to telescope within at least a portion of the activation member 60, which in turn, enables the overall injector assembly to be smaller and thus better able to fit within the user's palm and/or pocket, etc. Moreover, by making the sleeve 50 telescopic with respect to the activation member 60, the sleeve 50 may extend proximally with respect to the activation member 60 to a second position once the injector 10 has been activated. The sleeve 50 may re-encase the needle 33 after use to protect the user or other bystanders from accidentally contacting the needle 31 after discharge of the liquid/medication 33. Referring to FIGS. 4A-C and as will be described in greater detail below, in use, the sleeve 50 is moveably located with respect to the activation member 60 from a first position (as shown in FIG. 4A), in which the injector 10 is in the first, non-deployed configuration, to a second position (as shown in FIG. 4C), in which the injector 10 is in the third, depleted configuration. When the injector 10 is in the second, deployed configuration, the sleeve 50 is in a transitional position (as shown in FIG. 4B) between its first and second positions. As described herein, in the first position, the sleeve 50 interacts with or engages the activation member 60 to prevent the sleeve 50 from moving to its second position until the activation member 60 has moved to its second position. In the second position, the sleeve 50 interacts with or engages the activation member 60 in a second way to permanently prevent the sleeve 50 from moving back to its first position. In alternative embodiments, the sleeve 50 and activation member 60 may be formed as one integral member.

Referring to FIGS. 4A-C and 5, the sleeve 50 preferably includes at least one foot 51, and more preferably a pair of feet 51. The feet 51 are preferably located at the proximal end of the sleeve 50 and extend outwardly beyond the outer diameter of the sleeve 50. The feet may interact with and engage the proximal end of the activation member 60 to prevent the sleeve 50 from moving distally. When the activation member 60 is moved to its second position, during activation of the injector 10, the feet 51 interact with the body 20 at a shelf portion 27a. This interaction forces the feet 51 towards the inner diameter of the sleeve 50 causing the feet to disengage from the activation member 60 and allowing the sleeve 50 to move proximally to its second position. The feet 51 may have the shape of a right triangle, although other shapes conceivable in the art may be used. The portions of the feet 51 that face the outer diameter of the sleeve 50 are the hypotenuses of the triangles. The triangular shape of the feet 51 facilitate the inward movement of the feet 51 when they are engaging the shelf portion 27a of the body 20, and facilitate disengagement of the feet 51 from the activation member 60. The feet 51 may take on other forms, such as a half circle, or any other shape that interacts with the shelf to cause medial or lateral movement of the feet to allow for disengagement. Such shape may comprise, for example, an angled linear member or a curved member. The sleeve may also include at least one arm 52, and more preferably a pair of arms 52. In use, the arms 52 preferably extend outwardly beyond an outer diameter of the sleeve 50 so that when the sleeve 50 is biased proximately, the arms 52 interact with and engage cutout areas of the activation member 60 as described below. This interaction of the arms 52 with the cutout areas 52a of the activation member 60 occur when the sleeve 50 is in its second position, when the injector 10 is in the depleted configuration, and prevents the sleeve 50 from moving back to its first position.

Referring to FIGS. 4A-C and 5, the sleeve 50 preferably is sized and configured to be at least partially encased by the activation member 60. The activation member 60 may include one or more arms 61 and more preferably a pair of arms 61. Movement of the activation member 60 from the first position (as shown in FIG. 4A) to the second position (as shown in FIG. 4B) preferably deforms the crown 43, which preferably releases the plunger arm 42 to its second position. More specifically, movement of the activation member 60 from the first position to the second position causes the peripheral aspects of the crown 43 to move laterally away from the center of the injector 10 and distally towards the back of the injector. This lateral and distal movement of the lateral aspects of the crown 43 causes the crown 43 to disengage the plunger arm 42 and release it to its second position. Thus, movement of the activation member 60 from its first position to its second position causes the crown 43 to release the plunger arm 42, which thereby causes the plunger arm 42, the syringe 30 and the attached needle 31 to move proximally and causes the rubber plunger 32 to move proximally within the syringe 30, thus allowing the injector 10 to release the liquid/medication 33 from the syringe 30, through the needle 31, and into the patient, as will be described in greater detail below.

After injection of the liquid/medication 33 into the patient, the sleeve 50 moves from its first position, relative to the activation member 60, to its second position wherein the sleeve 50 re-encases the needle 31 to protect the user from accidentally contacting the needle 40 after discharge of the liquid/medication 33. More specifically, the injector 10 includes a second spring 55 (generally illustrated in FIGS. 4A-C) such as, for example, a second compression spring, which upon removing the injector 10 from the patient's skin, may bias the sleeve 50 proximally so that the sleeve 50 may re-encase the needle 31.

Moreover, the activation member 60 preferably includes one or more cutouts 52a so that when the sleeve 50 may be biased proximally to the second position, the aims 52 formed on the sleeve 50 interact with or engage the cutouts formed in the activation member 60 to thereby lock or secure the sleeve 50 in its second position to thereby protect the user from accidentally contacting the needle 31 after discharge of the liquid/medication. In addition, the sleeve 50 and the activation member 60 may include interacting grooves and/or projections to facilitate proper alignment of the sleeve 50 with the activation member 60 so that the arms 52 and the cutouts properly align.

As previously mentioned, the safety mechanism 70 may be sized and configured to protect the user from accidental discharge of the medicated liquid. The safety mechanism 70 prevents the crown 43 from deforming. The safety mechanism 70 thus also prevents the activation member 60 from moving to its second position because the activation member's movement is blocked by the crown 43 in its fixed position, and hence prevents the plunger arm 42, rubber plunger 32, syringe 30 and the needle 31 from moving to their second positions, which in turn prevents release of the liquid/medication. In this manner, the safety mechanism 70 may protect the user from accidental discharge of the medicated liquid. However, it should be appreciated that the safety mechanism 70 may take on any foam now or hereafter known as appreciated by one of ordinary skill in the art. For example, the safety mechanism 70 may be operatively associated with the activation member 60, the syringe 30 and/or the plunger arm 42 instead of the crown 43 to prevent the plunger arm 42, the syringe 30, and the needle 31 from proximally advancing.

Referring to FIGS. 1A-1E and 4A-C, the safety mechanism 70 may be in the shape of one or more depressible button(s) 72. More preferably, the injector 10 may include a pair of depressible buttons 72, one on either side of the stem 28 and needle 31. By providing a pair of buttons 72 on either side of the stem 28 and needle 31, the user may position the injector 10 into the palm of their hand with the stem 28, needle 31 and activation member 60, protruding between their fingers, which enables the user to simultaneously depress the buttons 72 and operate the injector 10 in a single, fluid motion with one hand. More specifically, the body 20 may be sized and configured to fit entirely within the palm of a user's hand such that the trailing surface 22 preferably abuts the user's palm while the stem 28, needle 31, and the activation member 60, with the enclosed sleeve 50 protrude in-between the user's fingers, which may engage the depressible buttons 72. This enables the user to activate the activation member 60 through a stabbing motion using the patient's palm as opposed to the patient's hand and/or fingers.

The injector 10 may also include a pair of springs 74 (generally illustrated in FIGS. 4A-C and 5) in operative contact with the pair of buttons 72, respectively, to bias the buttons 72 in their first position.

Activation of the safety mechanism 70 (e.g., depression of the buttons 72) enables the crown 43 to deform and thus may enable the activation member 60 to move from its first position to its second position. That is, referring to FIGS. 4A and 4B, the activation member 60 includes a first portion 66 that protrudes from the body 20, more specifically from the forward facing surface 21 and within the stem 28 of the body 20, to encase the needle 40, and a second portion 67, which resides in the internal cavity 27 of the body 20. As shown, the crown 43 is preferably in contact with the distal portion of the safety buttons 72 when they are in their first position, preventing the crown 43 from deforming. The second portion 67 of the activation member 60 is in contact with the crown 43. As previously mentioned, the activation member 60 may include one or more arms 61. The arms 61 of the activation member 60 may be operatively associated with the crown 43. Movement of the safety buttons 72 allows the movement of the activation mechanism 60 to its second position by leaving an open space on the outer edge of the crown 43 allowing the activation mechanism 60 to cause the crown 43 to deform.

Figure 2:
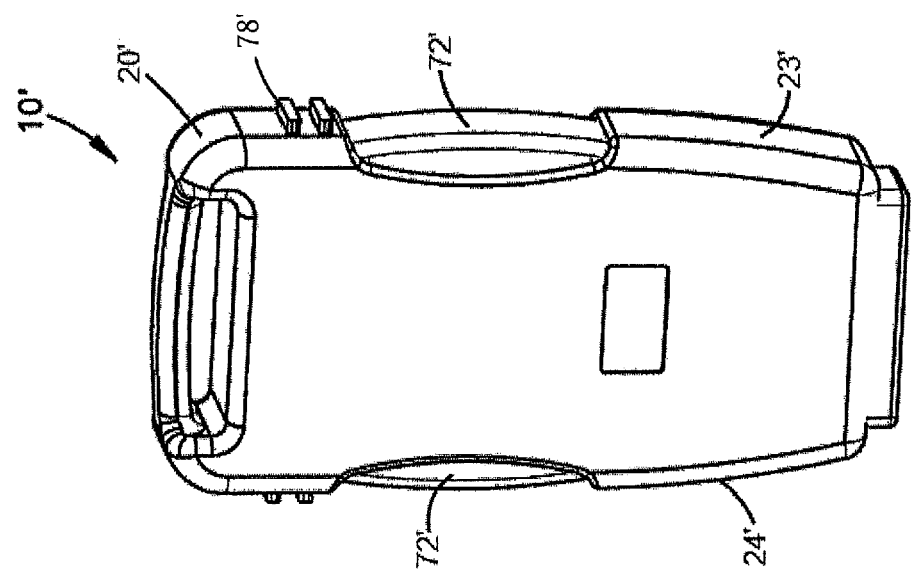
FIG. 2 is a perspective view of an injector according to an alternate embodiment of the present invention, the injector including depressible safety buttons on the side surfaces of the body.

In one embodiment, the buttons 72 are preferably configured so that they must be simultaneously depressed in order for the activation member 60 to move from its first position to its second position. In this manner, the user is better protected from accidental activation of the injector 10. It should be understood however that the buttons 72 may or may not require simultaneous depression. For example, the buttons 72 may require sequential depression in order to permit movement of the activation member 60. Moreover, the safety mechanism 70 may take on other forms and/or be located in other positions on the injector 10. For example, as shown in FIG. 2, the injector 10' may include one or more buttons 72' located on the side surfaces 23', 24' of the injector 10. Buttons 72' when depressed, may allow for movement of an activation member in order to deform a crown and release a first spring in the manner described above.

Referring to FIGS. 4A-C, in use, activation of the safety mechanism 70 (e.g., depression of the buttons 72) preferably causes the distal portions of the safety buttons 72 to vacate the space on each lateral side of the crown 43, wherein the safety buttons are preferably no longer in contact with the crown 43. This in turn may enable the activation member 60 to distally move from its first position to its second position by allowing the crown 43 to deform. Thus, depression of the safety buttons 72 allows the crown 43 to change shape such that subsequent movement of the activation member 60 to its second position deforms the crown 43 causing it to release the plunger arm 42, which thereby causes the plunger arm 42, the rubber plunger 33, the syringe 30 and attached needle 31 to move proximally resulting in the injector 10 releasing the liquid/medication from the syringe 30 through the needle 31 and into the patient.

In an alternate embodiment is shown in FIGS. 7A-7B and 8A-8B, in which injector 110 is generally similar to injector 10, including a body 120 having a front surface 121 and side surface 124, a spring 134, a safety mechanism 160, including buttons 162 and biasing springs 164, a stem 128 having threads 129 for attaching a cap 170. However, injector 110 includes activation member 152, which may include a cylindrical body 156 and one or more compressible portions 153, wherein each compressible portion 153 is operatively associated with one of the depressible buttons 162 so that in use, activation of the buttons 162 cause the compressible portions 153 to move or flex from a first position wherein the compressible portions 153 are in contact with one or more shelf portions 127a located inside the body 120 to a second position wherein the compressible portions 153 are free from the shelf portion 127a (e.g. the compressible portions no longer contact the shelf portions). Movement of the compressible portions 153 to their second position free the compressible portions 153 from the constraint of the shelf portions 127a and hence enable the activation member 152 to move distally.

In use, activation of the safety mechanism 160 (e.g., depression of the buttons 162) causes the compressible portions 153 formed on the activation member 152 to move from a first position wherein the compressible portions 153 are in contact with one or more shelf portions 127 a located inside the body 120 to a second position wherein the compressible portions 153 no longer contact the shelf portions 127a. This in turn enables the activation member 152 to distally move from its first position to its second position. Thus, depression of the safety buttons 162 frees the compressible portions 153 from the shelf portions 127 formed in the body 120 such that subsequent movement of the sleeve 150 to its second position may cause the activation member 152 to move to its second position wherein the compression portions 153 may contact one or more retention members 136 located within the internal cavity 127 of the body 120, which in turn causes the retention members 136 to release the plunger arm 132, which thereby causes the plunger arm 132, the syringe or cartridge (hereinafter "syringe") 142 and attached needle 140 to move proximally resulting in the injector 110 releasing the liquid or medication from the syringe 142 through the needle 140 to the user. Upon removal of the injector 110 from the patient's skin S, the second spring 155 biases the sleeve 150 to its second position so that the sleeve 150 re-encases the needle 140 to protect the user and others from accidental stabbing, etc.

In certain embodiments, the injector preferably may also include a threaded safety cap for providing additional assurance against accidental discharge. That is, as shown in FIGS. 1A-1E, the activation member preferably includes a plurality of threads 62 (threads 129 in FIGS. 7A-B) for threadably engaging the cap 80 (cap 170 in FIG. 7A). In use, the user initially unscrews the cap 80 to expose the activation member 60. The cap 80 may include one or more features that prevent the cap 80 from unintentionally unscrewing from the injector 10. The feature may be any feature now or hereafter known for such purpose including, but not limited to, placing a seal over the cap 80 that must be broken prior to unscrewing the cap 80, incorporating one or more breakable tabs on the cap 80, and that would need to be broken prior to the unscrewing the cap 80, and/or incorporating a latch mechanism, etc. The cap 80 may include one or more nubs 84 that align with a small indent formed on the body 20, more preferably on the stem 28. In use, the nubs 84 may click or snap into place when the cap 80 is screwed on. In one embodiment, in order to remove the cap 80, the user should initially apply additional pressure to disengage the nubs 84 from the indents in order to remove the cap 80. Moreover, the cap 80 preferably may include one or more indentations 82 to make it easier for the user to grip and unscrew the cap 80.

Figure 3:
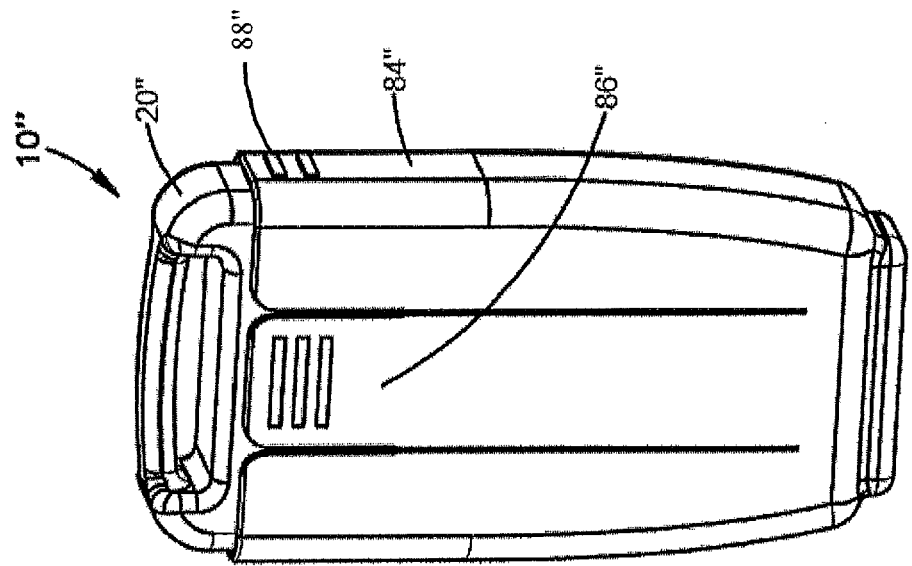
FIG. 3 is a perspective view of the injector of FIG. 2 including an outer casing for enclosing at least a portion of the body.

It should be understood, however, that the additional assurance mechanism may take on other forms. For example, the cap can be connected to the body by any other coupling mechanism now or hereafter known in the art including, for example, by snap-fitting, an interference fit, tamper-resistant or perforated cap etc. Moreover, as shown in FIG. 3, the additional assurance mechanism may be in the form of an outer casing 84" for enclosing at least a portion of the body 20". The outer casing 84" may include a tab 86" for allowing removable engagement of the body 20" and may further include recessed portions 88" for snap-fitting into protrusions 78" on the body 20". As illustrated in FIG. 2, the outer casing 84" may be removed from the injector 10' and thereby expose the safety mechanism 70.

In one embodiment, the needle 31 may preferably be covered by a protective sterile sheath 34 that allows for lasting sterility of the needle 31 and the liquid/medication. The sterile sheath 34 may have an inner soft aspect preferably made of rubber, and an outer firm aspect preferably made of plastic. The outer and inner aspects of the protective sheath 34 may connect to one another in a way that detachment from each other is unlikely. The cap 80 may also interact with or engage the outer firm aspect of the protective sheath 34 so that removal of the cap 80 also removes the sterile sheath 34. It should be understood however that additional strategies may be used, for example, the sterile sheath 34 may be made entirely of a soft material, preferably rubber. In alternative embodiments, removal of the cap 80 may not necessarily remove the protective sheath 34 but rather, the needle 31 may pierce and protrude through the protective sheath 34 during activation of the injector 10.

In certain embodiments, the injector 10 may be comprise dimensions including approximately 3.1-3.4 inches in length, including the body 20 and stem 28, and more preferably approximately 3.135-3.355 inches in length. The body 20 and stem 28 may be approximately 0.8-1.0 inches thick, from the forward facing surface to the trailing surface, and more preferably approximately 0.821-0.904 inches thick. The body 20 may have a width of approximately 1.5-1.7 inches, and more preferably 1.604-1.605 inches wide. The stem may have a width or diameter of approximately 0.8-0.9 inches, and more preferably approximately 0.845-0.868 inches wide.

One exemplary embodiment of a method of operating the injector 10 will now be described with continuing reference to FIGS. 1A-E and 4A-C. The user may remove the safety cap 80 thereby exposing the activation mechanism 60. The user may then activate the safety mechanism 70 (e.g. by depressing the buttons 72) and pressing the injector 10, more specifically a proximal end of the activation mechanism 60, against the patient's skin S. As previously described, by depressing the buttons 72, the space adjacent to the lateral aspects of the crown 43 are evacuated allowing the crown 43 to freely deform such that as the user presses the activation mechanism 60 against the patient's skin S, the activation mechanism 60 may move distally toward the trailing surface 22 of the body 20 to its second position. In moving to its second position, the activation mechanism 60 may cause the crown 43 to deform, which in turn may cause the syringe 30 and the attached needle 31 to move proximally and extend from the body 20, causing the plunger arm 42 to move proximally within the syringe 30 and thereby releasing the liquid from the syringe 30 through the needle 31 and into the patient. At this point, if the injector 10 alternatively includes a window 90, 91, the window 90, 91 may preferably show an indication that the injector 10 has been used. Upon removal of the injector 10 from the patient's skin S, the second spring 55 biases the sleeve 50 to its second position so that the sleeve 50 re-encases the needle 31 to protect the user and others from accidental stabbing, etc. In its second position, the arms 52 formed in the sleeve 50 may interact with or engage the cutouts 52a formed in the activation member 60 so that the sleeve 50 may lock or secure in the second position, thus re-encasing the needle 31.

It should be understood that those of ordinary skill in the art will recognize many modifications and substitutions may be made to various elements of the present invention. For example, various features and/or elements have been described in connection with the preferred embodiments, which have not been described in another preferred embodiment. It is envisioned that these features and/or elements are interchangeable such that a feature or element described in one embodiment may be used in combination with another embodiment.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the present description.

We claim:

1. An injector for delivering a liquid, the injector comprising:
   a body including a forward facing surface, and a trailing surface;
   a syringe assembly further comprising a chamber for containing liquid, and a needle extending toward the forward facing surface of the body;
   an activation mechanism moveably located with respect to the body from a first position to a second position;
   a protective sleeve operatively associated with the activation mechanism, the sleeve being moveably located with respect to the activation mechanism from a first position to a second position; and
   a safety mechanism moveably located with respect to the body from a first position to a second position,
   wherein the body has a stem extending from the forward facing surface thereof and is sized to fit in a user's hand with the stem extending between two fingers of the user's hand, and the safety mechanism includes two buttons, each of which extends from the forward facing surface on opposite sides of the stem, the buttons thus being simultaneously depressible by the user with the two fingers.

2. The injector of claim 1, wherein the injector is reconfigurable from a first, pre-deployed configuration to a second, deployed configuration and a third, depleted configuration, wherein the activation mechanism is in its first position when the injector is in the first, pre-deployed configuration and the activation mechanism is in its second position when the injector is in the second, deployed configuration and the activation mechanism is in its first position when the injector is in the third, depleted configuration.

3. The injector of claim 2, wherein when the safety mechanism is in the first position, the safety mechanism prevents the activation mechanism from moving to its second position, and while when the safety mechanism is in the second position, the safety mechanism enables the activation mechanism to move to its second position.

4. The injector of claim 3, wherein when the injector is in its first, pre-deployed configuration the protective sleeve is in its first position and when the injector is in the depleted configuration the sleeve is in its second position.

5. The injector of claim 1, wherein the injector is substantially key shaped, the body including a base having a width greater than that of the protective sleeve and configured such that the body may be held within a user's hand with the protective sleeve extending between the index and middle fingers.

6. The injector of claim 4, further comprising:
   a plunger arm in operative association with the syringe assembly, the plunger arm being moveably located within the body and with respect to the syringe assembly, the plunger arm being moveably located from a first position when the injector is in the pre-deployed configuration, to a second position when the injector is in the deployed configuration;
   a deformable member adjacent the plunger arm, the deformable member in a first shape when the injector is in the pre-deployed configuration, the deformable member preventing the plunger arm from moving to the plunger arm's second position when the deformable member is in its first shape, the deformable member capable of deforming to a second shape when the safety mechanism is in its second position, when in its second shape, the deformable member permitting the plunger arm to advance to its second position within the syringe assembly, proximally towards the forward facing surface of the body to cause the liquid from the syringe assembly to be released through the needle;
   wherein movement of the activation mechanism from the first position to the second position deforms the deformable member from the first shape, wherein the deformable member engages the plunger arm, to a second shape, wherein the deformable member releases the plunger arm.

7. The injector of claim 6, wherein the chamber and the needle are in operative association with the plunger arm so that the syringe assembly and the needle are moveably located with respect to the body from a first position, in which the needle point is not exposed beyond the body, when the injector is in the pre-deployed configuration, to a second position, in which the needle point is exposed beyond the body, when the injector is in the deployed configuration.

8. The injector of claim 7, wherein advancing the plunger arm proximally towards the forward facing surface of the body causes the plunger arm to move the syringe assembly towards the forward facing surface of the body.

9. The injector of claim 6, wherein the protective sleeve is moveably located with respect to the activation mechanism from its first position to a second position so that, after injection of the liquid, the sleeve re-encases the needle, the activation mechanism engaging the sleeve when the sleeve is in the second position so that the sleeve is secured with respect to the activation mechanism in the second position.

10. The injector of claim 9, wherein the injector further includes a first spring for biasing the plunger arm away from the trailing surface and a second spring biasing the sleeve to the second position.

11. The injector of claim 10, further comprising a power assembly capable of separate assembly, wherein the power assembly may be assembled separately to contain the first spring, alleviating the need to compress the spring during the final assembly of the injector.

12. The injector of claim 1, wherein the depressible buttons are configured so that they must be simultaneously depressed in order for the activation mechanism to move from its first position to its second position.

13. The injector of claim 12, wherein the injector further includes a deformable crown having lateral portions and wherein each depressible button contains a distal end that obstructs the lateral portions of the crown and prevent the crown from deforming;
  wherein the crown, when prevented from deforming, prevents the activation mechanism from moving from its first position to its second position.

14. The injector of claim 13, wherein when the depressible buttons are in their first position, distal ends of the depressible buttons obstruct the lateral portions of the crown, and while in their second position the distal ends evacuate the space lateral to the crown allowing the activation mechanism to forcibly deform the crown.

15. The injector of claim 1, wherein the injector further includes at least one dose of a liquid medicament.

16. The injector of claim 1, further comprising a removable cap and a sterile sheath, wherein when the cap is removed, the sterile sheath also detaches.

17. The injector of claim 1, wherein the sleeve is operably associated with the activation mechanism to prevent the sleeve from moving to its second position until the activation mechanism has moved to its second position.

18. The injector of claim 17, wherein the sleeve and the activation mechanism are an integrally formed member.

19. The injector of claim 17, wherein the body further comprises a shelf operably associated with the sleeve, the sleeve further comprising feet, whereby the shelf interacts with a portion of the feet such that movement of the activation mechanism to its second position causes medial movement of the feet that disengages the sleeve from the activation mechanism allowing the sleeve to move to its second position.

20. An injector for delivering a liquid, the injector reconfigurable from a pre-deployed configuration, to a deployed configuration, to a post-deployed configuration, the injector comprising:
  a body having a forward facing surface and a trailing surface, the body including a stem and an internal cavity for housing a syringe assembly;
  the syringe assembly including a container for containing liquid and a needle extending toward the forward facing surface of the body, the needle having a point;
  an activation mechanism moveably located with respect to the body from a first position, in which the activation mechanism extends proximally from the forward facing surface of the body, to a second position, in which the activation mechanism moves distally towards the trailing surface;
  a protective sleeve operatively associated with the activation mechanism, the sleeve being moveable from a first retracted position to a second extended position in which the sleeve extends beyond the needle; and
  a safety mechanism moveably located with respect to the body from a first position, in which the safety mechanism prevents the activation mechanism from moving to its second position, to a second position, in which the safety mechanism enables the activation mechanism to move to its second position, the safety mechanism including two buttons, each of which extends from the forward facing surface on opposite sides of the stem;
  wherein when the injector is in the pre-deployed configuration, the safety mechanism is in its first position, thereby preventing the activation mechanism from being in its second position;
  wherein when the injector is in the deployed configuration, the safety mechanism is in its second position, the activation mechanism is in its second position, and the needle point extends beyond the body and the sleeve for delivering the liquid; and
  wherein when the injector is in the post-deployed configuration, the sleeve is in its second position and extends beyond the needle point, thereby protecting a user from accidental contact with the needle point.

21. The injector of claim 20, wherein the stem extends from the forward facing surface and the body is sized to fit in a user's hand with the stem extending between two fingers of the user, the buttons thus being simultaneously depressible by the user with the two fingers.

22. The injector of claim 20, wherein the injector is substantially key shaped, the body having a width greater than that of the protective sleeve and configured such that the body may be held within a user's hand with the protective sleeve extending between the index and middle fingers.

23. The injector of claim 20, wherein the protective sleeve is moveably located with respect to the activation mechanism from its first position to a second position so that, after injection of the liquid, the sleeve re-encases the needle, the activation mechanism engaging the sleeve when the sleeve is in the second position so that the sleeve is secured with respect to the activation mechanism in the second position.

24. The injector of claim 20, wherein the depressible buttons are configured so that they must be simultaneously depressed in order for the activation mechanism to move from its first position to its second position.

25. The injector of claim 24, wherein the injector further includes a deformable crown having lateral portions and wherein each depressible button contains a distal end that obstructs the lateral portions of the crown and prevent the crown from deforming;

wherein the crown, when prevented from deforming, prevents the activation mechanism from moving from its first position to its second position.

26. The injector of claim 25, wherein when the depressible buttons are in their first position, distal ends of the depressible buttons obstruct the lateral portions of the crown, and while in their second position the distal ends evacuate the space lateral to the crown allowing the activation mechanism to forcibly deform the crown.

27. The injector of claim 20, wherein the injector further includes at least one dose of a liquid medicament.

28. The injector of claim 20, further comprising a power assembly capable of separate assembly, wherein the power assembly may be assembled separately to contain a compressed spring, alleviating the need to compress the spring during final assembly of the injector.

29. An injector for delivering a liquid, the injector reconfigurable from a pre-deployed configuration, to a deployed configuration, to a post-deployed configuration, the injector comprising:
- a body having a forward facing surface and a trailing surface, the body including an internal cavity for housing a syringe assembly;
- the syringe assembly including a container for containing liquid and a needle extending toward the forward facing surface of the body, the needle having a point;
- an activation mechanism moveably located with respect to the body from a first position, in which the activation mechanism extends proximally from the forward facing surface of the body, to a second position, in which the activation mechanism moves distally towards the trailing surface;
- a protective sleeve operatively associated with the activation mechanism, the sleeve being moveable from a first retracted position to a second extended position in which the sleeve extends beyond the needle; and
- a safety mechanism moveably located with respect to the body from a first position, in which the safety mechanism prevents the activation mechanism from moving to its second position, to a second position, in which the safety mechanism enables the activation mechanism to move to its second position;
- wherein when the injector is in the pre-deployed configuration, the safety mechanism is in its first position, thereby preventing the activation mechanism from being in its second position;
- wherein when the injector is in the deployed configuration, the safety mechanism is in its second position, the activation mechanism is in its second position, and the needle point extends beyond the body and the sleeve for delivering the liquid; and
- wherein when the injector is in the post-deployed configuration, the sleeve is in its second position and extends beyond the needle point, thereby protecting a user from accidental contact with the needle point;
- the injector further comprising:
- a plunger arm in operative association with the syringe assembly, the plunger arm being moveably located within the internal cavity of the body and with respect to the syringe assembly, the plunger arm being moveably located from a first position when the injector is in the pre-deployed configuration, to a second position when the injector is in the deployed configuration, and
- a crown adjacent the plunger arm, the crown in a first shape when the injector is in the pre-deployed configuration, the crown preventing the plunger arm from moving to the plunger arm's second position when the crown is in its first shape, the crown capable of deforming to a second shape when the safety mechanism is in its second position, when in its second shape, the crown permitting the plunger arm to advance to its second position within the syringe assembly, proximally towards the forward facing surface of the body to cause the liquid from the syringe assembly to be released through the needle.

30. The injector of claim 29, wherein movement of the activation mechanism from the first position to the second position deforms the crown from the first shape, wherein the crown engages the plunger arm, to a second shape, wherein the crown releases the plunger arm.

31. The injector of claim 29, wherein the container for containing liquid and the needle are in operative association with the plunger arm so that the syringe assembly and the needle are moveably located with respect to the body from a first position, in which the needle point is not exposed beyond the body, when the injector is in the pre-deployed configuration, to a second position, in which the needle point is exposed beyond the body, when the injector is in the deployed configuration.

32. The injector of claim 29, wherein advancing the plunger arm proximally towards the forward facing surface of the body causes the plunger arm to move the syringe assembly towards the forward facing surface of the body.

33. An injector for delivering a liquid, the injector reconfigurable from a pre-deployed configuration, to a deployed configuration, to a post-deployed configuration, the injector comprising:
- a body having a forward facing surface and a trailing surface, the body including an internal cavity for housing a syringe assembly;
- the syringe assembly including a container for containing liquid and a needle extending toward the forward facing surface of the body, the needle having a point;
- an activation mechanism moveably located with respect to the body from a first position, in which the activation mechanism extends proximally from the forward facing surface of the body, to a second position, in which the activation mechanism moves distally towards the trailing surface;
- a protective sleeve operatively associated with the activation mechanism, the sleeve being moveable from a first retracted position to a second extended position in which the sleeve extends beyond the needle; and
- a safety mechanism moveably located with respect to the body from a first position, in which the safety mechanism prevents the activation mechanism from moving to its second position, to a second position, in which the safety mechanism enables the activation mechanism to move to its second position;
- wherein when the injector is in the pre-deployed configuration, the safety mechanism is in its first position, thereby preventing the activation mechanism from being in its second position;
- wherein when the injector is in the deployed configuration, the safety mechanism is in its second position, the activation mechanism is in its second position, and the needle point extends beyond the body and the sleeve for delivering the liquid; and
- wherein when the injector is in the post-deployed configuration, the sleeve is in its second position and extends beyond the needle point, thereby protecting a user from accidental contact with the needle point;
- wherein the body further comprises a shelf operably associated with the sleeve, the sleeve further comprising feet, whereby the shelf interacts with a portion of the feet such that movement of the activation mechanism to its second position causes medial movement of the feet that disengages the sleeve from the activation mechanism allowing the sleeve to move to its second position.

34. An injector for delivering a liquid, the injector reconfigurable from a pre-deployed configuration, to a deployed configuration, to a post-deployed configuration, the injector comprising:
  a body having a forward facing surface and a trailing surface, the body including an extension from the forward facing surface and including an internal cavity for housing the liquid;
  a plunger assembly being moveably located within the internal cavity from a first position to a second position, the second position relatively away from the trailing surface, the plunger assembly biased in the second position;
  a needle in communication with the internal cavity and disposed within the body when the injector is in the pre-deployed configuration and extending beyond the body when the injector is in the deployed configuration;
  a deformable member located within the body, the deformable member being deformable from a first shape, in which the deformable member engages the plunger assembly to hold the plunger assembly in its first position, to a second shape, in which the deformable member releases the plunger assembly and permits the plunger assembly to move to its second position to cause the liquid to be released through the needle;
  an activation mechanism proximate the body extension, the activation mechanism distally moveable from a first position, in which the activation mechanism extends proximally from the body extension, to a second position, in which the activation mechanism moves distally towards the trailing surface;
  a protective sleeve operatively associated with the activation mechanism, the sleeve being moveably located from a first position to a second position, and
  first and second depressible safety buttons, each of the buttons extending from the forward facing surface of the body on opposite sides of the extension, each button biased in a first position and further depressible with respect to the forward facing surface from the first position, in which the deformable member is prevented from being deformed from its first shape to its second shape;
  wherein when the injector is in the pre-deployed configuration, the protective sleeve is in its first position, the safety buttons are in their first position, thereby preventing the activation mechanism from being in its second position and preventing the deformable member from being in its second position, the plunger assembly is in its first position and the needle is within the body;
  wherein when the injector is in the deployed configuration, the safety buttons are in their second position, the deformable member is in its second position, the activation mechanism is in its second position, the plunger assembly is in its second position and the needle extends beyond the body and the sleeve for delivering the liquid; and
  wherein when the injector is in the post-deployed configuration, the sleeve is in its second position and extends beyond the needle, thereby protecting a user from accidental contact with the needle.

35. The injector of claim 34, wherein the body has a stem extending from the forward facing surface thereof and is sized to fit in the user's hand with the stem extending between the two fingers of the user.

36. The injector of claim 34, wherein movement of the activation mechanism from the first position to the second position deforms the deformable member from the first shape, wherein the deformable member engages the plunger arm, to a second shape, wherein the deformable member releases the plunger arm.

37. The injector of claim 34, further comprising a syringe assembly wherein a container for containing liquid and the needle are in operative association with the plunger arm so that the syringe assembly and the needle are moveably located with respect to the body from a first position, in which the needle point is not exposed beyond the body, when the injector is in the pre-deployed configuration, to a second position, in which the needle point is exposed beyond the body, when the injector is in the deployed configuration.

38. The injector of claim 34, wherein the injector further includes a first spring for biasing the plunger arm away from the trailing surface and a second spring biasing the sleeve to the second position.

39. The injector of claim 34, wherein the deformable member, when prevented from deforming, prevents the activation mechanism from moving from its first position to its second position.

40. The injector of claim 34, wherein when the depressible buttons are in their first position, distal ends of the depressible buttons obstruct lateral portions of the deformable member, and while in their second position the distal ends evacuate the space lateral to the deformable member allowing the activation mechanism to forcibly deform the deformable member.

41. A method of delivering a liquid through an injector, the method comprising:
  providing an injector including a body, a sleeve, an activation mechanism, a safety cap, depressible buttons, a liquid containing chamber, a needle, a plunger arm, a first bias mechanism, and a second bias mechanism;
  removing a safety cap thereby exposing an activation mechanism;
  unlocking the activation mechanism by pressing depressible buttons;
  pressing the activation mechanism against a human's skin, wherein the activation mechanism moves from a first position to a second position, which releases the first bias mechanism which causes the liquid containing chamber and needle to move proximally such that the needle extends from the body and penetrates the human's skin, the bias mechanism further causing the plunger arm to move proximally within the liquid containing chamber and release the liquid from the liquid containing chamber through the needle into the human;
  removing the injector from the human's skin, permitting the second bias mechanism to bias the sleeve to extend so that substantially all of the needle is covered by the sleeve.

42. The method of claim 41, wherein the injector body includes an extension and the buttons include two buttons, one on each side of the extension, the method further including holding the injector in a single hand with the extension between two fingers and wherein pressing the buttons is performed with the two fingers.

* * * * *